United States Patent
Neighbors et al.

(10) Patent No.: US 12,427,133 B2
(45) Date of Patent: Sep. 30, 2025

(54) COMBINATION THERAPIES COMPRISING SCHWEINFURTHIN COMPOUNDS FOR TREATING CANCER

(71) Applicant: The Penn State Research Foundation, University Park, PA (US)

(72) Inventors: Jeffrey Neighbors, Hershey, PA (US); Todd Schell, Hershey, PA (US); Raymond Hohl, Hershey, PA (US); Joseph John Drabick, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 1039 days.

(21) Appl. No.: 16/969,481

(22) PCT Filed: Feb. 12, 2019

(86) PCT No.: PCT/US2019/017656
§ 371 (c)(1),
(2) Date: Aug. 12, 2020

(87) PCT Pub. No.: WO2019/157502
PCT Pub. Date: Aug. 15, 2019

(65) Prior Publication Data
US 2020/0405688 A1  Dec. 31, 2020

Related U.S. Application Data

(60) Provisional application No. 62/629,482, filed on Feb. 12, 2018.

(51) Int. Cl.
*A61K 31/353* (2006.01)
*A61K 39/395* (2006.01)
*A61P 35/00* (2006.01)

(52) U.S. Cl.
CPC ........ *A61K 31/353* (2013.01); *A61K 39/3955* (2013.01); *A61P 35/00* (2018.01)

(58) Field of Classification Search
CPC combination set(s) only.
See application file for complete search history.

(56) References Cited

U.S. PATENT DOCUMENTS 7,358,377 B2   4/2008   Wiemer et al.
7,902,228 B2   3/2011   Wiemer et al.
(Continued)

FOREIGN PATENT DOCUMENTS

WO   WO 2005/092878   10/2005

OTHER PUBLICATIONS

Topczewski JJ, Callahan MP, Kodet JG, Inbarasu JD, Mente NR, Beutler JA, Wiemer DF. Relevance of the C-5 position to schweinfurthin induced cytotoxicity. Bioorg Med Chem. Dec. 15, 2011;19(24):7570-81. doi: 10.1016/j.bmc.2011.10.034. Epub Oct. 19, 2011. PMID: 22055715; PMCID: PMC3232010. (Year: 2011).*

(Continued)

*Primary Examiner* — Adam Weidner
*Assistant Examiner* — Laura Ann Essex
(74) *Attorney, Agent, or Firm* — Fish & Richardson P.C.

(57) ABSTRACT

This document provides methods and materials for treating cancer. For example, methods and materials for using one or more schweinfurthin compounds and one or more immune-checkpoint inhibitors to treat a mammal having cancer are provided.

14 Claims, 5 Drawing Sheets

(56) References Cited

U.S. PATENT DOCUMENTS

| | | | |
|---|---|---|---|
| 8,637,685 B2 | 1/2014 | Wiemer et al. | |
| 9,428,493 B2* | 8/2016 | Kodet | A61P 43/00 |
| 2012/0095089 A1 | 4/2012 | Reilly et al. | |
| 2017/0015758 A1* | 1/2017 | Hammond | A61P 35/00 |
| 2017/0021019 A1 | 1/2017 | Zibelman et al. | |

OTHER PUBLICATIONS

Koubek EJ, Weissenrieder JS, Neighbors JD, Hohl RJ. Schweinfurthins: Lipid Modulators with Promising Anticancer Activity. Lipids. Aug. 2018;53(8):767-784. doi: 10.1002/lipd.12088. Epub Oct. 17, 2018. PMID: 30334267. (Year: 2018).*

Zhu Y, Xian X, Wang Z, Bi Y, Chen Q, Han X, Tang D, Chen R. Research Progress on the Relationship between Atherosclerosis and Inflammation. Biomolecules. Aug. 23, 2018;8(3):80. doi: 10.3390/biom8030080. PMID: 30142970; PMCID: PMC6163673. (Year: 2018).*

Atkins et al., "High-dose recombinant interleukin-2 therapy in patients with metastatic melanoma: Long-term survival update," The Cancer Journal from Scientific American, 2000, 6(1):S11-S14.

Atkins et al., "High-dose recombinant interleukin 2 therapy for patients with metastatic melanoma: analysis of 270 patients treated between 1985 and 1993," J. Clin, Oncology, Jul. 1999, 17(7):2105-2116.

Balch et al., "Final version of 2009 AJCC melanoma staging and classification," J. Clin. Oncology, Dec. 2009, 27(36):6199-6206.

Beutler et al., "Cytotoxic geranyl stilbenes from Macaranga schweinfurthii," J. Nat. Products, Dec. 1998, 61(12):1509-1512.

Beutler et al., "Schweinfurthin D, a cytotoxic stilbene from Macaranga schweinfurthii," Nat. Prod. Letters, Sep. 2000, 14(5):399-404.

Bracci et al., "Immune-based mechanisms of cytotoxic chemotherapy: implications for the design of novel and rationale-based combined treatments against cancer." Cell Death Differentiation, Jan. 2014, 21(1):15-25.

Cancer.gov [online], "Developmental Therapeutics Program: Obtain Vialed and Plated Compounds," available on or before Sep. 6, 2015 via Internet Archive: Wayback Machine URL<https://web.archive.org/web/20150906033641/https://dtp.cancer.gov/organization/dscb/obtaining/available_plates.htm>, retrieved on Nov. 5, 2020, retrieved from URL<https://dtp.cancer.gov/organization/dscb/obtaining/available_plates.htm>, 3 pages.

Cancer.org [online], "Cancer Facts & Figures 2017" available on or before Feb. 5, 2017, via Internet Archive: Wayback Machine URL<https://web.archive.org/web/20170205012952/https://www.cancer.org/content/dam/cancer-org/research/cancer-facts-and-statistics/annual-cancer-facts-and-figures/2017/cancer-facts-and-figures-2017.pdf> retrieved on Nov. 5, 2020, retrieved from URL<https://www.cancer.org/content/dam/cancer-org/research/cancer-facts-and-statistics/annual-cancer-facts-and-figures/2017/cancer-facts-and-figures-2017.pdf>, 76 pages.

Chapman et al., "Improved Survival with Vemurafenib in Melanoma with BRAF V600E Mutation," N. Engl. J. Medicine, Jun. 2011, 364(26): 2507-2516.

Cozza et al., "Protection from tumor recurrence following adoptive immunotherapy varies with host conditioning regimen despite initial regression of autochthonous murine brain tumors," Cancer Immunol. Immunotherapy, Mar. 2015, 64(3):325-336.

Davies et al., "Mutations of the BRAF gene in human cancer," Nature, Jun. 2002, 417(6892):949-954.

Day et al., "Tumor- and class-specific patterns of immune-related adverse events (irAEs) of immune checkpoint inhibitors (ICIs): A systematic review (SR)," J. Clin. Oncology, May 2016, 34(15):3065.

Dickson et al., "Staging and prognosis of cutaneous melanoma," Surg. Oncol. Clin. N. America, Jan. 2011, 20(1):1-17.

Flaherty et al., "Improved Survival with MEK Inhibition in BRAF-Mutated Melanoma," N. Engl. J. Medicine, Jul. 2012, 367(2):107-114.

Gajewski et al., "Innate and adaptive immune cells in the tumor microenvironment," Nat. Immunology, Oct. 2013, 14(10):1014-1022.

Galluzzi et al., "The secret ally: immunostimulation by anticancer drugs," Nat. Rev. Drug Discovery, Mar. 2012, 11(3):215-233.

Garbe et al., "Diagnosis and treatment of melanoma. European consensus-based interdisciplinary guideline—Update 2016," Eur. J. Cancer, Aug. 2016, 63:201-217.

Hauschild et al., "An update on BREAK-3, a phase III, randomized trial: Dabrafenib (DAB) versus dacarbazine (DTIC) in patients with BRAF V600E-positive mutation metastatic melanoma (MM)," J. Clin. Oncology, May 2013, 31(15S): Abstract No. 9013.

Hauschild et al., "Dabrafenib in BRAF-mutated metastatic melanoma: a multicentre, open-label, phase 3 randomised controlled trial," Lancet, Jun. 2012, 380(9839):358-365.

Hodi et al., "Improved Survival with Ipilimumab in Patients with Metastatic Melanoma," N. Engl. J. Medicine, Aug. 2010, 363(8):711-723.

Hodis et al., "A Landscape of Driver Mutations in Melanoma," Cell, Jul. 2012, 150(2):251-263.

Holstein et al., "Pleiotropic Effects of a Schweinfurthin on Isoprenoid Homeostasis," Lipids, Oct. 2011, 46(10):907-921.

Kepp et al., "Consensus guidelines for the detection of immunogenic cell death," Oncoimmunology, Sep. 2014, 3(9):e955691, 19 pages.

Khoja et al., "Tumour- and class-specific patterns of immune-related adverse events of immune checkpoint inhibitors: a systematic review," Ann. Oncology, Oct. 2017, 28(10):2377-2385.

Kokolus et al, "Schweinfurthin natural products induce regression of murine melanoma and pair with anti-PD-1 therapy to facilitate durable tumor immunity." Oncoimmunology, Nov. 2018, 8(2):e1539614, 13 pages.

Kuder et al., "Functional Evaluation of a Fluorescent Schweinfurthin: Mechanism of Cytotoxicity and Intracellular Quantification," Mol. Pharmacology, Jul. 2012, 82(1):9-16.

Kuder et al., "Schweinfurthins as novel anticancer agents," Thesis for the degree of Doctor of Philosophy, University of Iowa Graduate College, Dec. 2009, 173 pages.

Kuder et al., "Synthesis and biological activity of a fluorescent schweinfurthin analogue," Bioorg. Med. Chemistry, Jul. 2009, 17(13):4718-4723.

Larkin et al., "Combined Nivolumab and Ipilimumab or Monotherapy in Untreated Melanoma," N. Engl. J. Medicine, Jul. 2015, 373(1):23-34.

Long et al., "Dabrafenib and trametinib versus dabrafenib and placebo for Val600 BRAF-mutant melanoma: a multicentre, double-blind, phase 3 randomised controlled trial," Lancet, May 2015, 386(9992):444-451.

Long et al., "Increased MAPK reactivation in early resistance to dabrafenib/trametinib combination therapy of BRAF-mutant metastatic melanoma," Nat. Communications, Dec. 2014, 5:5694, 9 pages.

Luke et al., "Chemotherapy in the management of advanced cutaneous malignant melanoma," Clin. Dermatology, May 2013, 31(3):290-297.

Maio et al., "Five-Year Survival Rates for Treatment-Naive Patients With Advanced Melanoma Who Received Ipilimumab Plus Dacarbazine in a Phase III Trial," J. Clin. Oncology, Apr. 2015, 33(10):1191-1196.

Mente et al., "BF3 x Et2O-mediated cascade cyclizations: synthesis of schweinfurthins F and G," J. Org. Chemistry, Oct. 2008, 73(20):7963-7970.

Mente et al., "Total synthesis of (R,R,R)- and (S,S,S)-schweinfurthin F: differences of bioactivity in the enantiomeric series," Bioorg. Med. Chem. Letters, Feb. 2007, 17(4):911-915.

Michot et al., "Immune-related adverse events with immune checkpoint blockade: a comprehensive review," Eur. J. Cancer, Feb. 2016, 54:139-148.

Neighbors et al., "Synthesis and structure-activity studies of schweinfurthin B analogs: Evidence for the importance of a D-ring hydrogen bond donor in expression of differential cytotoxicity," Bioorg. Med. Chemistry, Mar. 2006, 14(6):1771-1784.

(56) References Cited

OTHER PUBLICATIONS

Neighbors et al., "Synthesis of nonracemic 3-deoxyschweinfurthin B," J. Org. Chemistry, Feb. 2005, 70(3):925-931.

Neighbors et al., "Synthesis of the cis-fused hexahydroxanthene system via cationic cascade cyclization," Tetrahedron Letters, Jul. 2009, 50(27):3881-3884.

Neighbors et al., "Synthesis of the schweinfurthin hexahydroxanthene core through Shi epoxidation," Tetrahedron Letters, Jan. 2008, 49(3):516-519.

PCT International Preliminary Report on Patentability in International Appln. No. PCT/US2019/017656, dated Aug. 18, 2020, 8 pages.

PCT International Search Report and Written Opinion in International Appln. No. PCT/US2019/017656, dated Jun. 7, 2019, 11 pages.

Rizos et al., "BRAF Inhibitor Resistance Mechanisms in Metastatic Melanoma: Spectrum and Clinical Impact," Clin. Cancer Research, Apr. 2014, A320(7):1965-1977.

Robert et al., "Improved Overall Survival in Melanoma with Combined Dabrafenib and Trametinib," N. Engl. J. Medicine, Jan. 2015, 372(1):30-39.

Robert et al., "Ipilimumab plus Dacarbazine for Previously Untreated Metastatic Melanoma," N. Engl. J. Medicine, Jun. 2011, 364(26):2517-2526.

Robert et al., "Nivolumab in Previously Untreated Melanoma without BRAF Mutation," N. Engl. J. Medicine, Jun. 2015, 372(4):320-330.

Robert et al., "Pembrolizumab versus Ipilimumab in Advanced Melanoma," N. Engl. J. Medicine, Jun. 2015. 372(26):2521-2532.

Schadendorf et al., "Three-year pooled analysis of factors associated with clinical outcomes across dabrafenib and trametinib combination therapy phase 3 randomised trials," Eur. J. Cancer, 2017. 82:45-55.

Schiavoni et al., "Cyclophosphamide Synergizes with Type I Interferons through Systemic Dendritic Cell Reactivation and Induction of Immunogenic Tumor Apoptosis," Cancer Research, Feb. 2011, 71(3):768-778.

Shi et al., "Acquired Resistance and Clonal Evolution in Melanoma during BRAF Inhibitor Therapy," Cancer Discovery, 2014. 4(1):80-93.

Skincancer.org [online], "Skin Cancer Facts & Statistics" available on or before Jan. 6, 2012 via Internet Archive: Wayback Machine URL <https://web.archive.org/web/20120106055038/http://www.skincancer.org/skin-cancer-information/skin-cancer-facts>, retrieved on Nov. 5, 2020, retrieved from URL<skincancer.org/skin-cancer-information/skin-cancer-facts>, 7 pages.

Sukkurwala et al., "Screening of novel immunogenic cell death inducers within the NCI Mechanistic Diversity Set," Oncoimmunology, Apr. 2014, 3(4).

Sunshine et al., "PD-1/PD-L1 inhibitors," Curr. Opin. Pharmacology, Aug. 2015, 23:32-38.

Sznol, "Betting on Immunotherapy for Melanoma," Curr. Oncol. Reports, Sep. 2009, 11(5):397-404.

Topczewski et al., "Exploration of cascade cyclizations terminated by tandem aromatic substitution: total synthesis of (+)-schweinfurthin A," J. Org. Chemistry, Feb. 2011, 76(3):909-919.

Topczewski et al., "First total synthesis of (+)-Vedelianin, a potent antiproliferative agent," Tetrahedron Letters, Apr. 2011, 52(14):1628-1630.

Topczewski et al., "Fluorescent schweinfurthin B and F analogs with anti-proliferative activity," Bioorg. Med. Chemistry, Sep. 2010, 18(18):6734-6741.

Topczewski et al., "Relevance of the C-5 position to schweinfurthin induced cytotoxicity," Bioorg. Med. Chemistry, Dec. 2011, 19(24):7570-7581.

Topczewski et al., "Total synthesis of (+)-schweinfurthins B and E," J. Org. Chemistry, Sep. 2009, 74(18):6965-6972.

Treadwell et al., "Synthesis of Schweinfurthin C, a geranylated stilbene from Macaranga schweinfurthii," J. Org. Chemistry, Nov. 1999, 64(23):8718-8723.

Turbyville et al., "Schweinfurthin A Selectively Inhibits Proliferation and Rho Signaling in Glioma and Neurofibromatosis Type 1 Tumor Cells in a NF1-GRD-Dependent Manner," Mol. Cancer Therapeutics, May 2010, 9(5): 1234-1243.

Ulrich et al., "Biologically active biotin derivatives of schweinfurthin F," Bioorg. Med. Chem. Letters, Nov. 2010, 20(22):6716-6720.

Ulrich et al., "Structural analogues of schweinfurthin F: probing the steric, electronic, and hydrophobic properties of the D-ring substructure;" Bioorg. Med. Chemistry, Feb. 2010, 18(4):1676-1683.

Van Allen et al., "The Genetic Landscape of Clinical Resistance to RAF Inhibition in Metastatic Melanoma," Cancer Discovery, Jan. 2014, 4(1):94-109.

Visiongain.com [online], "Market For Checkpoint Inhibitor Cancer Treatments Will Reach $16.55bn In 2020, According To New Visiongain Data," Sep. 13, 2018, retrieved on Nov. 5, 2020, retrieved from URL<https://www.visiongain.com/market-for-checkpoint-inhibitor-cancer-treatments-will-reach-16-55bn-in-2020-according-to-new-visiongain-data/>, 6 pages.

Ward-Kavanagh et al., "Whole-body irradiation increases the magnitude and persistence of adoptively transferred T cells associated with tumor regression in a mouse model of prostate cancer," Cancer Immunol. Research, Aug. 2014, 2(8):777-788.

Zhang et al., "Rapid determination of nine barbiturates in human whole blood by liquid chromatography-tandem mass spectrometer," Drug Test. Analysis, Apr. 2017, 9(4):588-595.

* cited by examiner

COMBINATION THERAPIES COMPRISING SCHWEINFURTHIN COMPOUNDS FOR TREATING CANCER

CROSS-REFERENCE TO RELATED APPLICATIONS

This application is a National Stage application under 35 U.S.C. § 371 of International Application No. PCT/US2019/017656, having an International Filing Date of Feb. 12, 2019, which claims priority to U.S. Provisional Patent Application Ser. No. 62/629,482, filed Feb. 12, 2018. The disclosure of the prior application is considered part of (and is incorporated by reference in) the disclosure of this application.

BACKGROUND

1. Technical Field

This document relates to methods and materials for treating cancer. For example, this document provides methods and materials for using one or more schweinfurthin compounds and one or more immune-checkpoint inhibitors to treat a mammal having cancer.

2. Background Information

It is estimated that there will be over 87,000 new cases of melanoma diagnosed in the United States in 2017, and that this will lead to approximately one death from this cancer every hour (Skin Cancer Foundation, "Skin Cancer Facts & Statistics" available at skincancer.org/skin-cancer-information/skin-cancer-facts; and American Cancer Society, "Cancer Facts & FIGS. 2017" available at cancer.org/content/dam/cancer-org/research/cancer-facts-and-statistics/annual-cancer-facts-and-figures/2017/cancer-facts-and-figures-2017.pdf). Melanoma is the deadliest of the skin cancers, and also represents almost 3% of pediatric cancers (American Cancer Society, "Cancer Facts & FIGS. 2017" available at cancer. org/content/dam/cancer-org/research/cancer-facts-and-statistics/annual-cancer-facts-and-figures/2017/cancer-facts-and-figures-2017.pdf). In the last 5 years, there has been a true revolution happening in the treatment options for melanoma. Before 2013, two treatment options existed, decarbazine chemotherapy (Luke et al., 2013 *Clinics in Dermatology*, 31:290-297) and an immunotherapy based on interleukin 2 (IL-2) (Atkins et al., 2000 *Cancer Journal from Scientific American*, 6:S11-S14; and Atkins et al., 1999 *Journal of Clinical Oncology*, 17:2105-2116), both of which were only modestly successful in disease management leaving the 5 year survival rate for advanced melanoma at around 10% (Balch et al., 2009 *Journal of Clinical Oncology*, 27:6199-6206; and Dickson et al., 2011 *Surgical Oncology Clinics of North America*, 20:1-17).

SUMMARY

This document provides methods and materials for treating cancer. For example, this document provides methods and materials for using one or more schweinfurthin compounds in combination with one or more immune-checkpoint inhibitors to treat a mammal having cancer. In some cases, one or more schweinfurthin compounds and one or more immune-checkpoint inhibitors can be administered together to a mammal having cancer to treat the mammal.

As demonstrated herein, a schweinfurthin compound can be used in combination with an immune-checkpoint inhibitor (e.g., an anti-PD-1 or anti-PD-L1 antibody) in a manner that results in a beneficial effect against cancer (e.g., melanoma) within a mammal. This beneficial effect can be greater than the anti-cancer effect observed in a comparable mammal receiving either the schweinfurthin compound alone or the immune-checkpoint inhibitor alone. Schweinfurthin compounds such as TTI-4242 and TTI-3114 each efficiently induced plasma membrane surface localization of the ER-resident protein calreticulin in treated B16.F10 melanoma cells, indicative of the induction of immunogenic cell death. In addition, schweinfurthin compounds such as TTI-4242 and TTI-3114 improved immune-checkpoint inhibitor-mediated immunotherapy (e.g., anti-PD-1-mediated or anti-PD-L1-mediated immunotherapy) of established tumors in mammals by delaying tumor progression and/or by triggering complete tumor regression. These results demonstrated that combining a schweinfurthin with an immune-checkpoint inhibitor enhances the anti-cancer immune response, leading to enhanced and durable anti-cancer immunity. The combined use of schweinfurthins and immune-checkpoint inhibitors as described herein can be used to improve response rates in cancers such as metastatic melanomas.

In general, one aspect of this document features a method for treating a mammal having cancer. The method comprises, or consists essentially of, administering one or more schweinfurthin compounds and one or more immune-checkpoint inhibitors to the mammal, wherein the number of cancer cells within the mammal is reduced. The mammal can be a human. The cancer can be a melanoma. The melanoma can be a metastatic melanoma. The one or more schweinfurthin compounds can be selected from the group consisting of TTI-4242, TTI-7106, TT1-3066, TTI-4242, schweinfurthin A, schweinfurthin B, schweinfurthin D, schweinfurthin E, schweinfurthin F, and schweinfurthin G The one or more schweinfurthin compounds can comprise TTI-4242, TTI-7106, or TT1-3066. The one or more immune-checkpoint inhibitors can be selected from the group consisting of anti-PD-1 antibodies, anti-PD-L1 antibodies, and anti-CTLA-4 antibodies. The one or more immune-checkpoint inhibitors can comprise an anti-PD-1 antibody or anti-PD-L1 antibody. The one or more schweinfurthin compounds and the one or more immune-checkpoint inhibitors can be administered to the mammal simultaneously. The one or more schweinfurthin compounds and the one or more immune-checkpoint inhibitors can be administered to the mammal simultaneously as a single composition comprising the one or more schweinfurthin compounds and the one or more immune-checkpoint inhibitors. The one or more schweinfurthin compounds and the one or more immune-checkpoint inhibitors can be administered to the mammal at different times. The one or more schweinfurthin compounds can be administered to the mammal before the one or more immune-checkpoint inhibitors are administered to the mammal. The one or more schweinfurthin compounds can be administered to the mammal after the one or more immune-checkpoint inhibitors are administered to the mammal.

In another aspect, this document features a method for treating a mammal having cancer. The method comprises, or consists essentially of, administering one or more schweinfurthin compounds and one or more immune-checkpoint inhibitors to the mammal, wherein the survival time of the mammal from the cancer is increased as compared to the survival time of a comparable mammal not administered the one or more schweinfurthin compounds and one or more immune-checkpoint inhibitors. The mammal can be a human. The cancer can be a melanoma. The melanoma can be a metastatic melanoma. The one or more schweinfurthin compounds can be selected from the group consisting of TTI-4242, TTI-7106, TT1-3066, TTI-4242, schweinfurthin A, schweinfurthin B, schweinfurthin D, schweinfurthin E, schweinfurthin F, and schweinfurthin G The one or more schweinfurthin compounds can comprise TTI-4242, TTI-7106, or TT1-3066. The one or more immune-checkpoint inhibitors can be selected from the group consisting of anti-PD-1 antibodies, anti-PD-L1 antibodies, and anti-CTLA-4 antibodies. The one or more immune-checkpoint inhibitors can comprise an anti-PD-1 antibody or anti-PD-L1 antibody. The one or more schweinfurthin compounds and the one or more immune-checkpoint inhibitors can be administered to the mammal simultaneously. The one or more schweinfurthin compounds and the one or more immune-checkpoint inhibitors can be administered to the mammal simultaneously as a single composition comprising the one or more schweinfurthin compounds and the one or more immune-checkpoint inhibitors. The one or more schweinfurthin compounds and the one or more immune-checkpoint inhibitors can be administered to the mammal at different times. The one or more schweinfurthin compounds can be administered to the mammal before the one or more immune-checkpoint inhibitors are administered to the mammal. The one or more schweinfurthin compounds can be administered to the mammal after the one or more immune-checkpoint inhibitors are administered to the mammal.

In another aspect, this document features a method for treating a mammal at risk of developing cancer. The method comprises, or consists essentially of, administering one or more schweinfurthin compounds and one or more immune-checkpoint inhibitors to the mammal, wherein time to developing cancer within the mammal is increased as compared to time to developing cancer within a comparable mammal not administered the one or more schweinfurthin compounds and one or more immune-checkpoint inhibitors. The mammal can be a human. The one or more schweinfurthin compounds can be selected from the group consisting of TTI-4242, TTI-7106, TT1-3066, TTI-4242, schweinfurthin A, schweinfurthin B, schweinfurthin D, schweinfurthin E, schweinfurthin F, and schweinfurthin G The one or more schweinfurthin compounds can comprise TTI-4242, TTI-7106, or TT1-3066. The one or more immune-checkpoint inhibitors can be selected from the group consisting of anti-PD-1 antibodies, anti-PD-L1 antibodies, and anti-CTLA-4 antibodies. The one or more immune-checkpoint inhibitors can comprise an anti-PD-1 antibody or anti-PD-L1 antibody. The one or more schweinfurthin compounds and the one or more immune-checkpoint inhibitors can be administered to the mammal simultaneously. The one or more schweinfurthin compounds and the one or more immune-checkpoint inhibitors can be administered to the mammal simultaneously as a single composition comprising the one or more schweinfurthin compounds and the one or more immune-checkpoint inhibitors. The one or more schweinfurthin compounds and the one or more immune-checkpoint inhibitors can be administered to the mammal at different times. The one or more schweinfurthin compounds can be administered to the mammal before the one or more immune-checkpoint inhibitors are administered to the mammal. The one or more schweinfurthin compounds can be administered to the mammal after the one or more immune-checkpoint inhibitors are administered to the mammal.

In another aspect, this document features a composition comprising, or consisting essentially of, one or more schweinfurthin compounds and one or more immune-checkpoint inhibitors. The one or more schweinfurthin compounds can be selected from the group consisting of TTI-4242, TTI-7106, TT1-3066, TTI-4242, schweinfurthin A, schweinfurthin B, schweinfurthin D, schweinfurthin E, schweinfurthin F, and schweinfurthin G The one or more schweinfurthin compounds can comprise TTI-4242, TTI-7106, or TT1-3066. The one or more immune-checkpoint inhibitors can be selected from the group consisting of anti-PD-1 antibodies, anti-PD-L1 antibodies, and anti-CTLA-4 antibodies. The one or more immune-checkpoint inhibitors can comprise an anti-PD-1 antibody or anti-PD-L1 antibody. The one or more schweinfurthin compounds and the one or more immune-checkpoint inhibitors can be the sole active ingredients against cancer cells of the composition.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
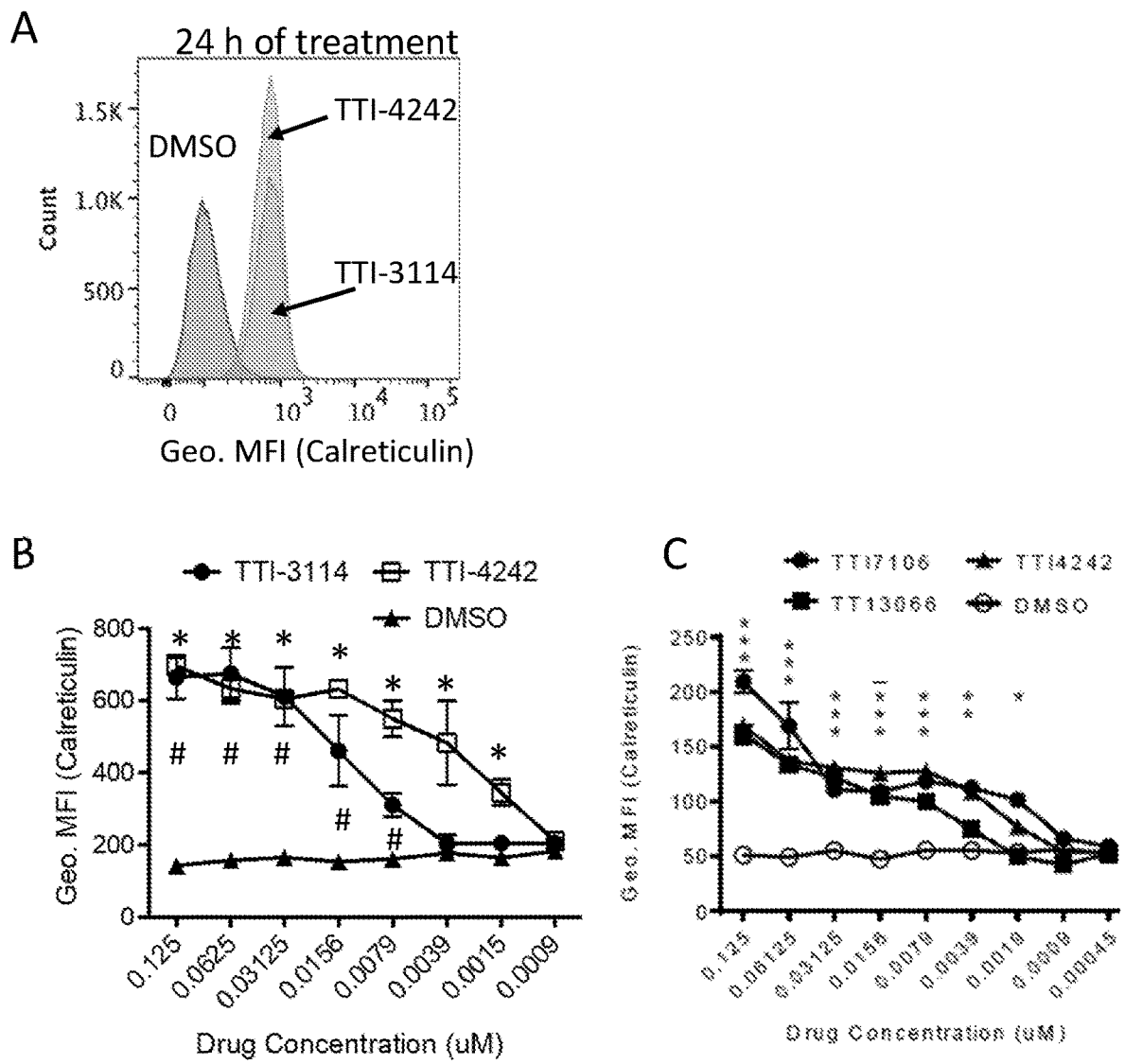
FIG. 1 shows that schweinfurthin compounds induce significant expression of surface calreticulin. B16.F10 cells were cultured with increasing concentrations of schweinfurthin compounds or DMSO control for 24 hours. Surface calretuculin was measured by flow cytometry. (A) Representative flow cytometry histograms. (B) Points represent three replicate concentrations of TTI-4242 or TTI-3114 +/− standard error. (C) Points represent three replicate concentrations of TTI-7106, TT1-3066, or TTI-4242 +/− standard error. The results are representative of two independent experiments. Significance was determined by two-way ANOVA with Bonferoni post-tests and are shown for values that are $p<0.01$. *, TTI-4242 vs. control; #, TTI-3114 vs. control.

This document provides methods and materials for treating cancer. For example, this document provides methods and materials for using one or more schweinfurthin compounds and one or more immune-checkpoint inhibitors to treat a mammal (e.g., a human) having cancer (e.g., melanoma). In some cases, a combination of one or more schweinfurthin compounds and one or more immune-checkpoint inhibitors can be administered to a mammal having cancer to reduce proliferation or progression of cancer cells within the mammal and/or to induce or increase the mammal's anti-cancer immune response to treat the mammal. In some cases, a combination of one or more schweinfurthin compounds and one or more immune-checkpoint inhibitors can be administered to a mammal to reduce the number, frequency, or severity of one or more (e.g., two, three, four, or five) signs or symptoms of a cancer in a mammal having a cancer, to induce cancer regression (e.g., reduce the number of cancer cells and/or reduce the size of a tumor), to reduce tumor growth or metastasis, and/or to reduce the proliferative, migratory, and/or invasive potential of cancer cells.

Using a combination of one or more schweinfurthin compounds and one or more immune-checkpoint inhibitors to treat cancer can result in a beneficial effect (e.g., increased survival, increased cancer-free survival, reduced cancer progression, and/or increased time to cancer recurrence) that is greater than the anti-cancer effect observed in a comparable mammal receiving either the schweinfurthin compound alone or the immune-checkpoint inhibitor alone. In some cases, a combination of one or more schweinfurthin compounds and one or more immune-checkpoint inhibitors can be administered to a mammal to reduce a mammal's risk of developing a cancer and/or of experiencing a cancer recurrence. For example, one or more schweinfurthin compounds and one or more immune-checkpoint inhibitors can be administered to a mammal at risk of developing a cancer to reduce the proliferation and/or progression of pre-cancerous cells within the mammal.

Any appropriate mammal having cancer or at risk of developing cancer can be treated as described herein (e.g., by administering one or more schweinfurthin compounds and one or more immune-checkpoint inhibitors). Examples of mammals that can be treated as described herein include, without limitation, humans or other primates (such as monkeys), dogs, cats, horses, cows, pigs, sheep, mice, and rats. For example, a human having cancer can be treated by administering one or more schweinfurthin compounds and one or more immune-checkpoint inhibitors to the mammal.

When treating a mammal (e.g., a human) having a cancer or at risk of developing a cancer as described herein (e.g., by administering one or more schweinfurthin compounds and one or more immune-checkpoint inhibitors), the cancer can be any appropriate cancer. In some cases, a cancer can be a primary cancer. In some cases, a cancer can be a metastatic cancer. Examples of cancers that can be treated as described herein include, without limitation, melanoma, brain cancer, breast cancer, colorectal cancer, kidney cancer, endometrial cancer, prostate cancer, testicular cancer, thyroid cancer, and osteosarcoma. For example, a human having a metastatic melanoma can be treated by administering one or more schweinfurthin compounds and one or more immune-checkpoint inhibitors.

In some cases, the methods and materials described herein can include identifying a mammal as having cancer or as being at risk of developing a cancer. Any appropriate method can be used to identify a mammal having cancer. For example, imaging techniques and biopsy techniques can be used to identify mammals (e.g., humans) having cancer. Any appropriate method can be used to identify a mammal as being at risk of developing a cancer. For example, biopsy techniques can be used to identify mammals (e.g., humans) having pre-cancerous cells. In some cases, genotyping techniques and/or examination of a mammal's medical history can be used to identify a mammal as being at risk of developing a cancer.

Once a mammal is identified as having a cancer (e.g., melanoma) or as being at risk of developing a cancer, the mammal can be treated as described herein. For example, a mammal having cancer (e.g., melanoma) or at risk of developing cancer can be administered or instructed to self-administer one or more schweinfurthin compounds and one or more immune-checkpoint inhibitors. Administration of one or more schweinfurthin compounds and one or more immune-checkpoint inhibitors can be effective to treat the mammal. For example, one or more schweinfurthin compounds and one or more immune-checkpoint inhibitors can be administered to a human having metastatic melanoma to treat the human.

A schweinfurthin compound used as described herein can be any appropriate schweinfurthin compound. For example, a schweinfurthin compound can be a schweinfurthin compound that can perturb cellular cholesterol homeostasis in a cell (e.g., pre-cancerous cell or a cancer cell). In some cases, a schweinfurthin compound can be a natural schweinfurthin compound, a synthetic schweinfurthin compound, or a schweinfurthin analog. Examples of schweinfurthin compounds include, without limitation, TTI-4242, TTI-7106, TT1-3066, TTI-4242, schweinfurthin A, schweinfurthin B, schweinfurthin D, schweinfurthin E, schweinfurthin F, schweinfurthin G, and analogs thereof.

Chemical structures of several schweinfurthin compounds that can be used as described herein are as shown below:

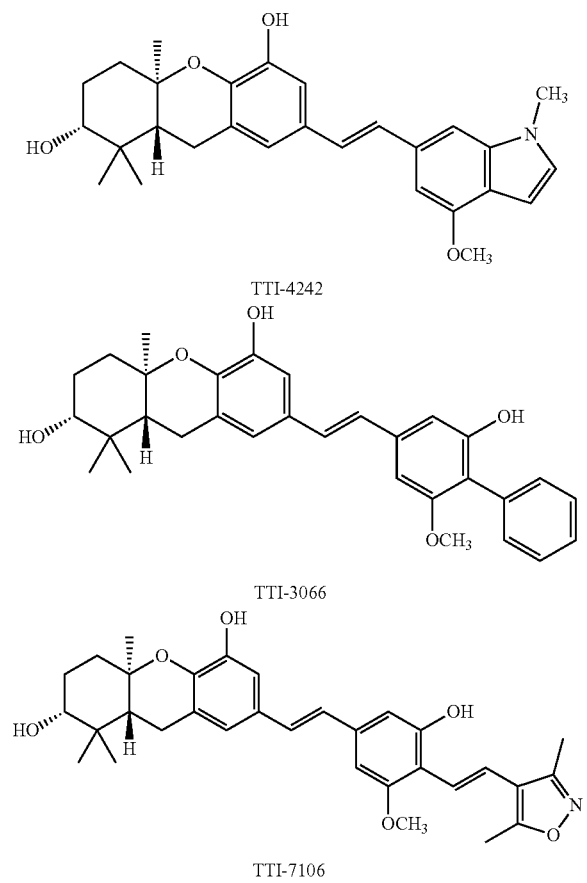

In some cases, a schweinfurthin compound used in combination with one or more immune-checkpoint inhibitors as described herein can have the following structure:

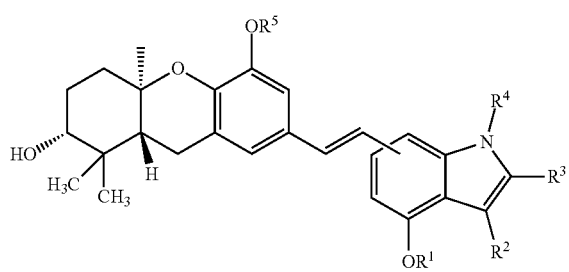

$R^1$ is H or $(C_1-C_6)$alkyl;
$R^2$ is H, fluoro, $(C_1-C_{15})$alkyl, $(C_2-C_{15})$alkenyl, aryl, or heteroaryl, wherein any aryl or heteroaryl is optionally substituted with one or more groups independently selected from halo, nitro, trifluoromethyl, trifluoromethoxy, nitro, cyano, $(C_1-C_6)$alkyl, $(C_3-C_6)$cycloalkyl, $(C_3-C_6)$ cycloalkyl$(C_1-C_6)$alkyl, $(C_1-C_6)$alkoxy, $(C_1-C_6)$alkanoyl, $(C_1-C_6)$alkoxycarbonyl, and $(C_2-C_6)$ alkanoyloxy; and wherein any $(C_1-C_{15})$alkyl, and $(C_2-C_{15})$alkenyl of $R^2$ is optionally substituted with azetidino, aziridino, pyrrolidino, piperidino, piperazino, morpholino, tetrahydrofuranyl, tetrahydrothiophenyl, $(C_3-C_6)$cycloalkyl, or $NR_aR_b$;
$R^3$ is H, $(C_1-C_{15})$alkyl, or $(C_2-C_{15})$alkenyl;
$R^4$ is H or $(C_1-C_6)$alkyl;
$R^5$ is H or $(C_1-C_6)$alkyl;
each $R_a$ and $R_b$ is independently H or $(C_1-C_6)$alkyl;
or a salt thereof (e.g., a pharmaceutically acceptable salt thereof).

In some cases, a schweinfurthin compound used in combination with one or more immune-checkpoint inhibitors as described herein can have the following structure:

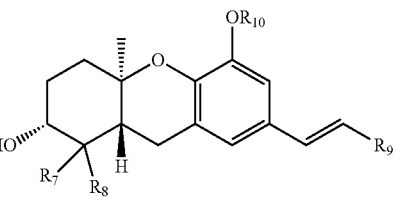

$R_7$ and $R_8$ are each independently H or $(C_1-C_6)$ alkyl;
$R_9$ is H, $(C_1-C_{15})$alkyl, $(C_2-C_{15})$alkenyl, $(C_2-C_{15})$alkynyl, $(C_1-C_{15})$alkoxy, $(C_1-C_{15})$alkanoyl, $(C_1-C_{15})$alkoxycarbonyl, $(C_2-C_{15})$alkanoyloxy, aryl or heteroaryl, which aryl or heteroaryl is optionally substituted with one or more halo, hydroxy, cyano, $CF_3$, $OCF_3$, $NR^aR^b$, $(C_1-C_{15})$alkyl, $(C_2-C_{15})$alkenyl, $(C_2-C_{15})$alkynyl, $(C_1-C_{15})$ alkoxy, $(C_1-C_{15})$alkanoyl, $(C_1-C_{15})$alkoxycarbonyl, $(C_1-C_{15})$alkoxy$(C_1-C_{15})$alkoxy, —P(=O)(OH)$_2$, and $(C_2-C_{15})$alkanoyloxy;
$R_{10}$ is H or $(C_1-C_6)$ alkyl; and
$R^a$ and $R^b$ are each independently H or $(C_1-C_6)$alkyl wherein any $(C_1-C_{15})$alkyl, $(C_2-C_{15})$alkenyl, $(C_2-C_{15})$ alkynyl, $(C_1-C_{15})$alkoxy, $(C_1-C_{15})$alkanoyl, $(C_1-C_{15})$ alkoxycarbonyl, or $(C_2-C_{15})$alkanoyloxy of $R_7$, $R_8$, and $R_9$ is optionally substituted with one or more halo, hydroxy, cyano, or oxo (=O); or a salt thereof (e.g., a pharmaceutically acceptable salt thereof).

In some cases, a schweinfurthin compound used in combination with one or more immune-checkpoint inhibitors as described herein can be as described elsewhere (see, e.g., Beutler et al., *J. Nat. Prod.,* 61:1509-12 (1998); Beutler et al., *Natural Product Letters,* 14:399-404 (2000); Treadwell et al., *Journal of Organic Chemistry,* 64:8718-8723 (1999); Mente et al., *Biorganic & Medicinal Chemistry Letters,* 17:911-915 (2007); Mente et al., *Journal of Organic Chemistry,* 73:7963-7970 (2008); Topczewski et al., *Journal of Organic Chemistry,* 74:6965-6972 (2009); Topczewski et al., *Journal of Organic Chemistry,* 76:909-919 (2011); Topczewski et al., *Tetrahedron Letters,* 52: 1628-1630 (2011); Topczewski et al., *Bioorganic & Medicinal Chemistry,* 18:6734-6741 (2010); Ulrich et al., *Bioorganic & Medicinal Chemistry,* 18:1676-1683 (2010); Neighbors et al., *Journal of Organic Chemistry,* 70:925-931 (2005); Kuder et al., *Biorganic & Medicinal Chemistry Letters,* 17:4718-23 (2009); Neighbors et al., *Tetrahedron Letters,* 49:516-519 (2008); Neighbors et al., *Bioorganic & Medicinal Chemistry,* 14:1771-1784 (2006); Neighbors et al., *Tetrahedron Letters,* 50:3881-3884 (2009); Kuder et al., *Bioorganic &*

*Medicinal Chemistry*, 17:4718-4723 (2009); Ulrich et al., *Bioorganic & Medicinal Chemistry Letters*, 20:6716-6720 (2010); Topczewski et al., *Bioorganic & Medicinal Chemistry*, 19:7570-7581 (2011); U.S. Pat. Nos. 7,358,377; 7,902,228; 9,428,493; and International Patent Application Publication No. WO 2005/092878).

An immune-checkpoint inhibitor used as described herein can be any appropriate immune-checkpoint inhibitor. For example, an immune-checkpoint inhibitor used as described herein can be a molecule that inhibits expression or activity (e.g., signaling) of an immune-checkpoint polypeptide. Examples of compounds that can be used as immune-checkpoint inhibitors described herein include, without limitation, proteins (e.g., antibodies), small molecules, nucleic acid molecules designed to induce RNA interference (e.g., siRNA molecules or shRNA molecules), antisense molecules, and miRNAs. Examples of immune-checkpoint polypeptides include, without limitation, programmed cell death protein (PD-1), programmed death ligand 1 (PD-L1), programmed death ligand 2 (PD-L2), and cytotoxic T-lymphocyte-associated protein 4 (CTLA-4). In some cases, an immune-checkpoint inhibitor used as described herein can be an antibody that inhibits PD-1/PD-L1 signaling. For example, an anti-PD-1 antibody (e.g., nivolumab, pembrolizumab, and pidilizumab) or an anti-PD-L1 antibody (e.g., 10F.9G2, atezolizumab, avelumab, and durvalumab) can be used as an immune-checkpoint inhibitor to treat cancer as described herein. In some cases, an immune-checkpoint inhibitor used as described herein can be an antibody that inhibits CTLA-4/B7-1 and/or CTLA-4/B7-2 signaling. For example, an anti-CTLA-4 antibody (e.g., ipilimumab) can be used as an immune-checkpoint inhibitor to treat cancer as described herein. In some cases, an immune-checkpoint inhibitor can be designed based upon the nucleic acid and/or polypeptide sequences of an immune-checkpoint polypeptide. Nucleic acid and/or polypeptide sequences of immune-checkpoint polypeptides (e.g., PD-1, PD-L1, and CTLA-4) can be as described elsewhere (see, e.g., the National Center for Biotechnology Information (NCBI) sequence databases).

This document also provides compositions (e.g., anti-cancer compositions) containing one or more schweinfurthin compounds described herein and/or one or more immune-checkpoint inhibitors described herein. For example, a combination of one or more schweinfurthin compounds and one or more immune-checkpoint inhibitors to treat a mammal having cancer (or at risk of developing cancer) as described herein can be formulated into a single composition for administration to the mammal. Such a single composition can include one or more schweinfurthin compounds and one or more immune-checkpoint inhibitors as the sole active ingredients. In some cases, a composition including one or more schweinfurthin compounds and one or more immune-checkpoint inhibitors can include one or more other anti-cancer agents. Examples of other anti-cancer agents that can be formulated into a composition having one or more schweinfurthin compounds and one or more immune-checkpoint inhibitors include, without limitation, abraxane, acalabrutinib, alemtuzumab, bevacizumab, bortezomib, carboplatin, cisplatin, cetuximab, paclitaxel, rituximab, tamoxifen citrate, taxol, and trastuzumab.

In some cases, a combination of one or more schweinfurthin compounds and one or more immune-checkpoint inhibitors to treat a mammal having cancer (or at risk of developing cancer) as described herein can be formulated into separate compositions that are administered to the mammal simultaneously or serially (e.g., not administered simultaneously). In such cases, one composition can be formulated to include one or more schweinfurthin compounds, and another composition can be formulated to include one or more immune-checkpoint inhibitors. A composition formulated to include one or more schweinfurthin compounds can be formulated to include the one or more schweinfurthin compounds as the sole active ingredients for that composition. A composition formulated to include one or more immune-checkpoint inhibitors can be formulated to include the one or more immune-checkpoint inhibitors as the sole active ingredients for that composition. In some cases, a composition including one or more schweinfurthin compounds and/or a composition including one or more immune-checkpoint inhibitors can include one or more other anti-cancer agents described herein. When administered serially, a composition containing one or more schweinfurthin compounds can be administered to a mammal having cancer (or at risk of developing cancer) before a composition containing one or more immune-checkpoint inhibitors is administered. In some cases, a composition containing one or more immune-checkpoint inhibitors can be administered to a mammal having cancer (or at risk of developing cancer) before a composition containing one or more schweinfurthin compounds is administered.

A composition described herein (e.g., a composition containing one or more schweinfurthin compounds, a composition containing one or more immune-checkpoint inhibitors, or a composition containing one or more schweinfurthin compounds and one or more immune-checkpoint inhibitors) can be formulated into a pharmaceutical composition. For example, a composition described herein can be formulated together with one or more pharmaceutically acceptable carriers (additives), pharmaceutical diluents, and/or pharmaceutical excipients. The term "pharmaceutically acceptable" refers to a generally non-toxic, inert, and/or physiologically compatible composition. Pharmaceutically acceptable carriers (additives), pharmaceutical diluents, and/or pharmaceutical excipients include materials such as adjuvants, carriers, pH-adjusting and buffering agents, tonicity adjusting agents, wetting agents, preservatives, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A composition described herein (e.g., a composition containing one or more schweinfurthin compounds, a composition containing one or more immune-checkpoint inhibitors, or a composition containing one or more schweinfurthin compounds and one or more immune-checkpoint inhibitors) can be formulated for administration in solid or liquid form including, without limitation, sterile solutions, suspensions, sustained-release formulations, tablets, capsules, pills, creams ointments, powders, and granules.

A composition described herein (e.g., a composition containing one or more schweinfurthin compounds, a composition containing one or more immune-checkpoint inhibitors, or a composition containing one or more schweinfurthin compounds and one or more immune-checkpoint inhibitors) can be designed for topical, oral, parenteral (including subcutaneous, intramuscular, intravenous, and intradermal), or intratumoral administration. Compositions suitable for parenteral administration can include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a composition described herein (e.g., a composition containing one or more schweinfurthin compounds, a composition containing one or more immune-checkpoint inhibitors, or a composition containing one or more schweinfurthin compounds and one or more immune-checkpoint inhibitors) can be administered locally (e.g., intratumorally) or systemically. For example, a composition described herein can be administered locally by injection into tumors or into biological spaces infiltrated by tumors (e.g. peritoneal cavity and/or pleural space). In some cases, a composition provided herein can be administered systemically, orally, or by injection to a human.

In some cases, a combination of one or more schweinfurthin compounds and one or more immune-checkpoint inhibitors can be administered to a mammal having cancer or a mammal at risk of developing cancer as a combination therapy with one or more additional cancer treatments. The one or more cancer treatments that can be used in combination with one or more schweinfurthin compounds and one or more immune-checkpoint inhibitors can include any appropriate cancer treatment. Examples of such cancer treatments that can be used in combination with one or more schweinfurthin compounds and one or more immune-checkpoint inhibitors include, without limitation, surgery, radiation therapy, the administration of a pharmacotherapy such as a chemotherapy, hormone therapy, targeted therapy, and/or cytotoxic therapy. In cases where one or more schweinfurthin compounds and one or more immune-checkpoint inhibitors described herein are used in combination with one or more cancer treatments, the one or more cancer treatments can be administered at the same time or independently. For example, a composition including one or more schweinfurthin compounds and one or more immune-checkpoint inhibitors can be administered first, and the one or more cancer treatments can be administered second, or vice versa. In some cases, a composition including one or more schweinfurthin compounds can be administered first followed by one or more other cancer treatments that are followed by administration of a composition including one or more immune-checkpoint inhibitors.

One or more schweinfurthin compounds and one or more immune-checkpoint inhibitors can be administered in an amount, at a frequency, and for a duration effective to treat a mammal (e.g., a human) having cancer or a mammal (e.g., a human) at risk of developing cancer. Effective doses can vary depending on the risk and/or the severity of the cancer, the route of administration, the age and general health condition of the mammal, excipient usage, the possibility of co-usage with other therapeutic treatments such as use of other agents, and the judgment of the treating physician.

An effective amount of a schweinfurthin compound and/or an immune-checkpoint inhibitor for use as described herein can be any amount that reduces the severity of cancer without producing significant toxicity to the mammal. For example, an effective amount of a schweinfurthin compound (e.g., TTI-4242, TTI-7106, or TTI-3114) can be from about 0.5 mg/kg to about 500 mg/kg. In some cases, an effective amount of a schweinfurthin compound (e.g., TTI-4242, TTI-7106, or TTI-3114) can be from about 1 mg/kg to about 250 mg/kg (e.g., from about 5 mg/kg to about 250 mg/kg, from about 10 mg/kg to about 250 mg/kg, from about 20 mg/kg to about 250 mg/kg, from about 5 mg/kg to about 200 mg/kg, from about 5 mg/kg to about 150 mg/kg, from about 5 mg/kg to about 100 mg/kg, from about 5 mg/kg to about 50 mg/kg, or from about 20 mg/kg to about 40 mg/kg). In some cases, an effective amount of an immune-checkpoint inhibitor (e.g., an anti-PD-1 antibody, an anti-PD-L1 antibody, or anti-CTLA-4 antibody) can be from about 0.5 mg/kg to about 100 mg/kg (e.g., from about 1 mg/kg to about 100 mg/kg, from about 5 mg/kg to about 100 mg/kg, from about 0.5 mg/kg to about 75 mg/kg, from about 0.5 mg/kg to about 50 mg/kg, from about 0.5 mg/kg to about 25 mg/kg, from about 0.5 mg/kg to about 10 mg/kg, from about 0.5 mg/kg to about 5 mg/kg, or from about 1 mg/kg to about 5 mg/kg). The effective amount of a schweinfurthin compound and/or an immune-checkpoint inhibitor can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and risk and/or severity of the cancer may require an increase or decrease in the actual effective amount administered. If a particular mammal fails to respond to a particular amount of a schweinfurthin compound and/or an immune-checkpoint inhibitor, then the amount of the schweinfurthin compound and/or immune-checkpoint inhibitor can be increased (e.g., by two-fold, three-fold, four-fold, or more). After receiving this higher amount, the mammal can be monitored for both responsiveness to the treatment and toxicity symptoms, and adjustments made accordingly.

The frequency of administration of a schweinfurthin compound and/or an immune-checkpoint inhibitor can be any frequency that reduces the severity of cancer without producing significant toxicity to the mammal. For example, the frequency of administration of a schweinfurthin compound and/or an immune-checkpoint inhibitor can be from about two to about three times a week to about two to about three times a year. In some cases, a mammal having cancer can receive a single administration of a schweinfurthin compound and repeated administrations of an immune-checkpoint inhibitor, or vice versa. The frequency of administration of a schweinfurthin compound and/or an immune-checkpoint inhibitor can remain constant or can be variable during the duration of treatment. A course of treatment with a schweinfurthin compound and/or an immune-checkpoint inhibitor can include rest periods. For example, a schweinfurthin compound and an immune-checkpoint inhibitor can be administered every other month over a two-month period followed by a six-week rest period, and such a regimen can be repeated multiple times. In cases where a first composition including one or more schweinfurthin compounds and a second composition including one or more immune-checkpoint inhibitors are used, the frequency of administration of the first composition and the frequency of administration of the second composition can be the same or the frequency of administration of the first composition and the frequency of administration of the second composition can be independent of each other. For example, a composition including one or more schweinfurthin compounds (e.g., TTI-4242, TTI-7106, or TTI-3114) can be administered daily, and a compound including one or more immune-checkpoint inhibitors (e.g., an anti-PD-1 antibody, an anti-PD-L1 antibody, or an anti-CTLA-4 antibody) can be administered twice per week. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a schweinfurthin compound and/or an immune-checkpoint inhibitor can be any duration that reduces the severity of cancer without producing significant toxicity to the mammal. In some cases, the effective duration can vary from several months to several years. In general, the effective duration for treating a cancer present within a mammal can range in duration from about one or two months to five or more years. In cases where a composition including one or more schweinfurthin compounds and a composition including one or more immune-checkpoint inhibitors are used, the effective durations for administering the two compositions can be the same or the effective durations for administering the two compositions can be independent of each other. For example, a composition including one or more schweinfurthin compounds (e.g., TTI-4242, TTI-7106, or TTI-3114) can be administered at a particular frequency over a duration of about 2 weeks, and a composition including one or more immune-checkpoint inhibitors (e.g., an anti-PD-1 antibody, an anti-PD-L1 antibody, or an anti-CTLA-4 antibody) can be administered at a particular frequency over a duration of about 6-12 months. Multiple factors can influence the actual effective duration used for a particular treatment. For example, an effective duration can vary with the frequency of administration, effective amount, use of multiple treatment agents, route of administration, and severity of the condition being treated.

In some cases, one or more schweinfurthin compounds (e.g., TTI-4242, TTI-7106, or TTI-3114) can be administered at about 1 mg/kg to about 30 mg/kg (e.g., about 20 mg/kg) daily for about 5 to about 25 days, and one or more immune-checkpoint inhibitors (e.g., an anti-PD-1 antibody, an anti-PD-L1 antibody, or an anti-CTLA-4 antibody) can be administered at about 1 mg/kg to about 5 mg/kg (e.g., about 2 mg/kg) once every three weeks for about 6 months to the lifetime of the mammal (e.g., human).

In certain instances, a mammal can be monitored for cancer to evaluate the effectiveness of the cancer treatment. Any appropriate method can be used to determine whether or not the cancer present within a mammal is treated. For example, imaging techniques or laboratory assays can be used to assess the number of cancer cells and/or the size of a tumor present within a mammal. For example, imaging techniques or laboratory assays can be used to assess the location of cancer cells and/or a tumor present within a mammal.

Also provided herein are kits that include a composition described herein (e.g., a composition containing one or more schweinfurthin compounds, a composition containing one or more immune-checkpoint inhibitors, or a composition containing one or more schweinfurthin compounds and one or more immune-checkpoint inhibitors). In some cases, a kit provided herein can include instructions for performing any of the methods described herein. In some cases, a kit provided herein can include at least one dose of a composition described herein (e.g., a composition containing one or more schweinfurthin compounds, a composition containing one or more immune-checkpoint inhibitors, or a composition containing one or more schweinfurthin compounds and one or more immune-checkpoint inhibitors). In some cases, a kit provided herein can include a device (e.g., a syringe) for administering a composition described herein (e.g., a composition containing one or more schweinfurthin compounds, a composition containing one or more immune-checkpoint inhibitors, or a composition containing one or more schweinfurthin compounds and one or more immune-checkpoint inhibitors).

The invention will be further described in the following examples, which do not limit the scope of the invention described in the claims.

EXAMPLES

Example 1: Schweinfurthin Compounds Combine with Anti-PD-1 Immunotherapy to Control Established Murine Melanoma To investigate whether schweinfurthins improve existing cancer immunotherapies (e.g., by inducing initial tumor cell death that could lead to stronger or more sustained anti-tumor immune responses), the ability of schweinfurthins to promote immunogenic cell death in melanoma tumor cells and to impact anti-PD-1 immunotherapy in immune competent mice was evaluated.

Materials and Methods

Evaluation of Calreticulin Expression:

B16.F10 melanoma cells were plated at $1.5$-$2.0 \times 10^5$ cells per well in 24-well plates in RPMI-1640 medium containing standard supplements and 10% fetal bovine serum (FBS) and incubated overnight at 37° C., 5% $CO_2$. Compounds solubilized in dimethyl sulfoxide (DMSO) were added at the indicated concentrations and incubated for a further 24 hours at 37° C., 5% $CO_2$. Control wells were treated with similar dilutions of DMSO. Cells were trypsinized and washed with FACS buffer (2% FBS+0.1% $NaN_3$ in PBS) and seeded at $1$-$2 \times 10^5$ per well in 96-well round-bottom plates. Cells were stained with rabbit anti-calreticulin polyclonal antibody (1:100, Abcam ab2907) in FACS buffer for 30 minutes at 4° C. Following two washes, cells were labeled with goat anti-rabbit Alexa Fluor 488 (1:500, Thermo Fisher A11070) in FACS buffer for 30 minutes at 4° C. Cells were washed twice and labeled with 7-aminoactinomyosin D in order to exclude non-viable cells. Samples were immediately run on a BD LSR Fortessa flow cytometer and the data analyzed using FlowJo software.

Treatment of Mice and In Vivo Tumor Growth Analysis:

Groups of 8-week old C57BL/6J female mice were inoculated with $1 \times 10^5$ freshly cultured B16.F10 tumor cells subcutaneously in the left flank. Mice were monitored for the development of tumors and when palpable were randomized into groups. Mice received αPD-1 (clone RMP1-14; BioXCell) or control rat IgG (Sigma) at 200 µg/day intraperitoneally in a volume of 200 µl PBS twice per week for 3 weeks. Mice received daily TTI-4242 or TTI-3114 at 30 mg/kg/day or vehicle only for 5 consecutive days in a total volume of 100 µL. Tumors were measured with digital calipers and the tumor volume calculated as (length× $width^2$)/2. Mice were euthanized when the tumor volume exceeded 1500 $mm^3$, developed ascites or necrosis, or when mice became lethargic. When indicated, mice that exhibited complete tumor regressions were re-challenged with $\kappa \times 10^5$ freshly cultured B16.F10 tumor cells subcutaneously in the left flank and tumor development was monitored.

Histology:

Mice were euthanized and tumors were dissected from the mice (where applicable). In mice with full tumor regression, tissue underlying where the tumor had been growing was collected. This surrounding tissue was visually inspected for pigmentation. Formalin fixed paraffin embedded (FFPE) sections were used. Briefly, excised tissue was immersed in 10% neutral buffered formalin for at least 24 hours followed by transfer into 70% ethanol for at least 24 hours. Tissue was embedded in paraffin, and 6 µm sections stained with hematoxylin and eosin (H&E) in the Penn State College of Medicine Comparative Medicine histology core lab. Stained sections were evaluated by a board certified dermatopathologist who was blinded to the sample identification. Images were collected on an Olympus BX51 Microscope using cellSense standard software.

Statistics:

Differences in tumor growth curves were evaluated by linear mixed models for longitudinal analysis and Kaplan-Meier survival curves were evaluated by log rank test. Differences in calreticulin expression were determined by two-way ANOVA with Bonferroni post-test. All data were analyzed using Graphpad Prism (version 7) or SAS (version 9.4) software.

Results

TTI Compounds Induce Immunogenic Tumor Cell Death in Murine Melanoma Cells In Vitro.

The dose response of calreticulin expression on B16.F10 melanoma cells, derived from C57BL/6 mice, to the schweinfurthin compounds TTI-4242 and TTI-3114 was evaluated. Both compounds induced surface calreticulin following 24 hours of treatment (FIG. 1A). TTI-3114 induced high levels of surface calreticulin expression at concentrations above 8 nM while TTI-4242 maintained this effect even below 2 nM (FIG. 1B). These results identify the schweinfurthin compounds as potent inducers of immunogenic cell death, suggesting that they may synergize with immunotherapy for melanoma in vivo.

Figure 2:
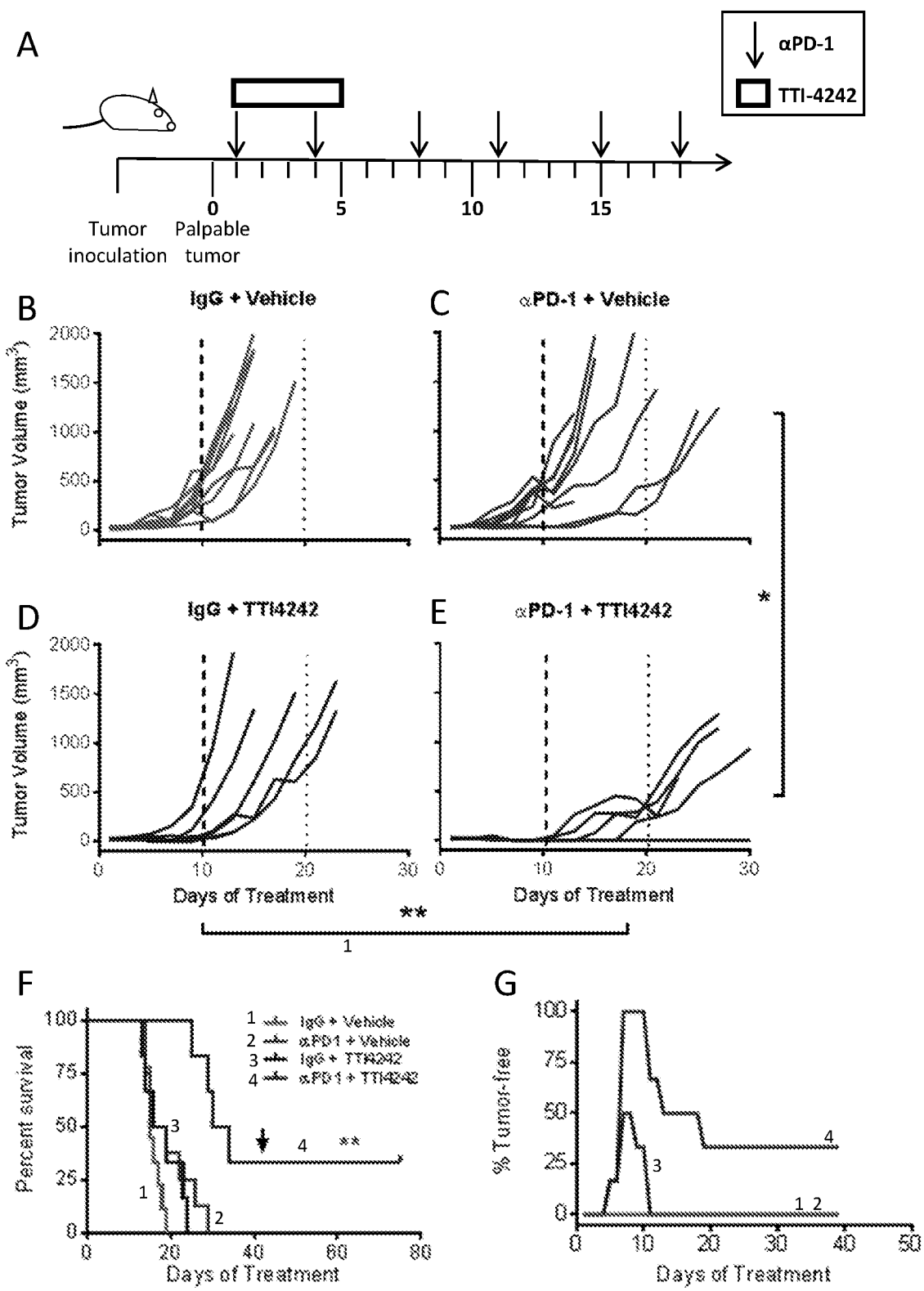
FIG. 2 shows that TTI-4242 improves tumor control in mice treated with anti-PD-1 therapy. (A) Experimental schema; B16.F10 tumor-bearing mice received 200 µg of anti-PD-1 antibody twice a week for three weeks and/or 40 µg TTI-4242 for five consecutive days. Controls mice received 200 µg rat IgG or an equivalent volume of vehicle. Mice were treated with (B) IgG and vehicle, (C) anti-PD-1 antibody and vehicle, (D) IgG and TTI-4242, and (E) anti-PD-1 antibody and TTI-4242. Days 10 and 20 are indicated with long- and short-dashed lines. N=6-9/group; p values determined by mixed linear models; pairwise comparisons are indicated: *$p<0.05$; $p<0.01$. (F) Kaplan-meier survival analysis. (G) The percentage of mice tumor-free in each treatment group. N=6-9/group; p values determined by log rank test; pairwise comparison between anti-PD-1 antibody plus TTI-3114 and all other groups: $p<0.01$.

TTI-4242 Administration Improves Anti-PD-1 Therapy to Delay Melanoma Progression and Induce Durable Anti-Tumor Immunity The following was performed to determine if schweinfurthin compounds alter the efficacy of antibody-based anti-PD-1 (αPD-1) immunotherapy, a standard immunotherapy used to treat patients with metastatic melanoma that improves the anti-tumor T cell response by blocking the interaction of the PD-1 inhibitory receptor with its ligand on tumor cells and antigen presenting cells. C57BL/6 mice were implanted with B16.F10 cells subcutaneously. Once tumors became palpable, mice were randomized into four treatment groups: (1) control IgG+Vehicle, (2) αPD-1+Vehicle, (3) IgG+TTI-4242, (4) αPD-1+TTI-4242. Antibodies for PD-1 or control IgG were administered twice a week for a total of 6 treatments, and TTI-4242 or vehicle control was administered for the first five consecutive days (FIG. 2A). It was observed that neither αPD-1 alone (FIG. 2C) nor TTI-4242 alone (FIG. 2D) impacted tumor growth rate compared to control treated mice (FIG. 2B). When αPD-1 and TTI-4242 were provided in a combined therapeutic regimen (FIG. 2E), tumor growth was significantly delayed compared to αPD-1 alone (FIG. 2C) and TTI-4242 alone (FIG. 2D). In addition, mice receiving dual αPD-1 and TTI-4242 lived significantly longer than mice in all other treatment groups (FIG. 2F). It also was observed that 50% and 100% of tumors in the TTI-4242 alone and αPD-1+TTI-4242 groups, respectively, showed initial tumor regression during the period of TTI-4242 administration (FIG. 2G). After 42 days, two mice (33.3%) in the combined therapy group remained tumor-free, and receipt of a second dose of $5 \times 10^5$ B16.F10 tumor cells at this late time point did not result in new tumor growth (FIGS. 2F-G). Taken together, these findings demonstrate that αPD-1 and TTI-4242 work together to provide a greater anti-tumor response than either treatment alone, in some cases leading to complete tumor cures and protective immunity to re-challenge.

Figure 3:
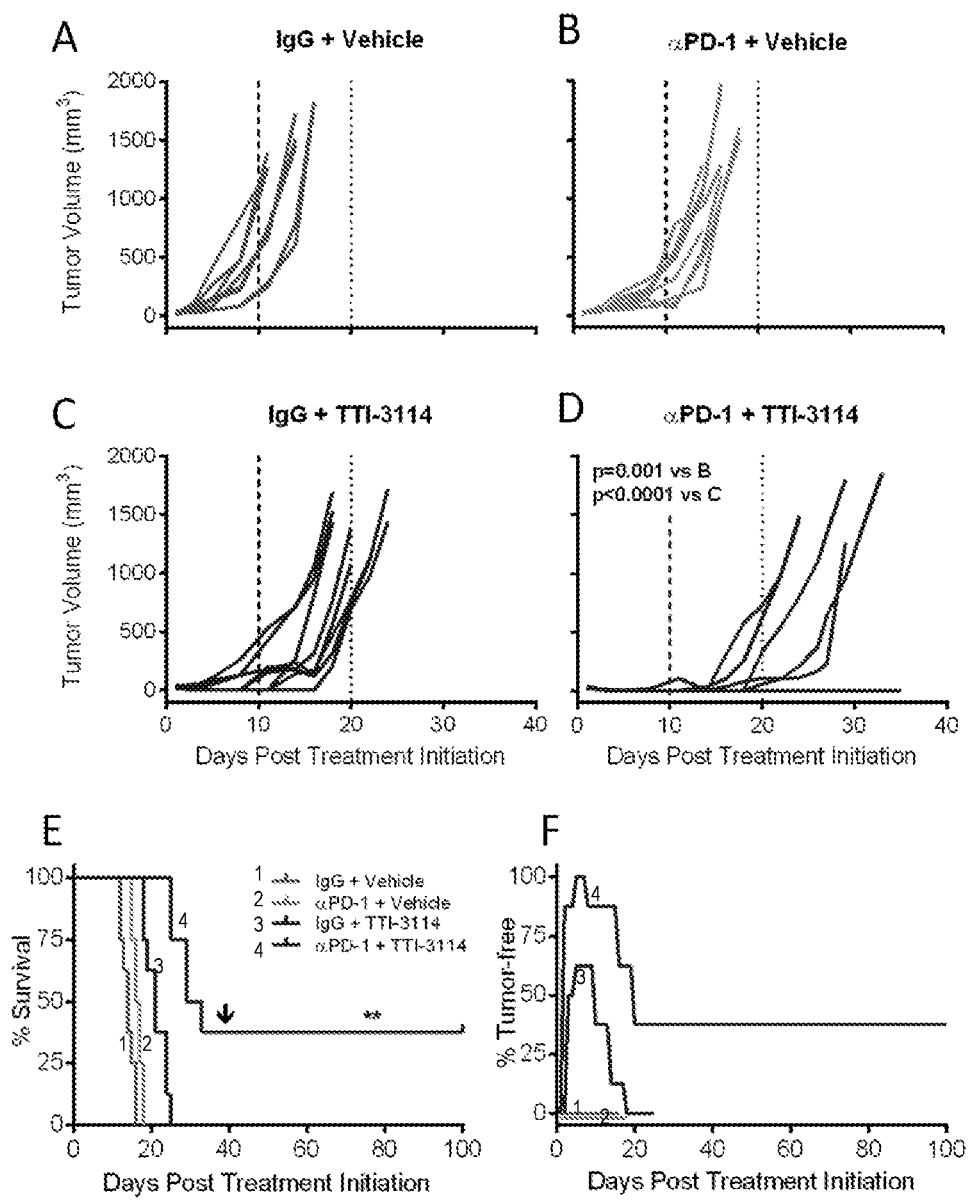
FIG. 3 shows that TTI-3114 in combination with anti-PD-1 antibody delays tumor growth. Mice were treated according to the schedule in FIG. 2A using TTI-3114 (20 mg/kg). Once tumors became palpable (~20 mm³), mice were treated with (A) IgG and vehicle, (B) anti-PD-1 antibody and vehicle, (C) IgG and TTI-4242, (D) anti-PD-1 antibody and TTI-4242. Days 10 and 20 are indicated with long- and short-dashed lines. N=6-9/group; p values determined by mixed linear models and shown for pairwise comparisons to anti-PD-1 antibody+TTI-3114. (E) Kaplan-meier survival analysis. Arrow indicates the day of challenge (day 39). N=6-9/group; p values determined by log rank test; pairwise comparisons between αPD-1+TTI-4242 and all other groups: **$p<0.01$. (F) The percentage of mice tumor-free (no palpable or visually apparent tumor) in each treatment group. The experiment was terminated at 100 days post treatment initiation at which point all surviving mice were tumor free.

TTI-3114 Administration Improves αPD-1 Therapy Against Established B16.F10 Melanoma To extend the in vivo results beyond a single schweinfurthin compound, the efficacy of TTI-3114 with anti-PD-1 therapy of B16.F10 tumors was tested since this compound showed a similar, although less potent effect on immunogenic cell death in vitro. Similar to the experimental design depicted in FIG. 2A, B16.F10 tumor-bearing mice were treated with αPD-1 in combination with TTI-3114. In a similar fashion to what was observed with TTI-4242 (FIG. 2), it was found that dual αPD-1+TTI-3114 treatment (FIG. 3D) significantly delayed tumor growth compared to αPD-1 alone (FIG. 3B) or TTI-3114 alone (FIG. 3C). This combination therapy also significantly extended survival compared to control mice or those treated with either monotherapy (FIG. 3E). Similar to the results with TTI-4242, 60% and 100% of mice that received TTI-3114 alone or in combination with αPD-1, respectively, showed initial tumor regression, and three mice (37.5%) remained tumor free at 36 days post treatment initiation (FIG. 3F). Thus, two different compounds within the same class of schweinfurthins improved immunotherapy against an aggressive murine melanoma and resulted in some durable complete responses.

TTI-3114 Treatment is Associated with Lymphocytic Infiltration

Figure 4:
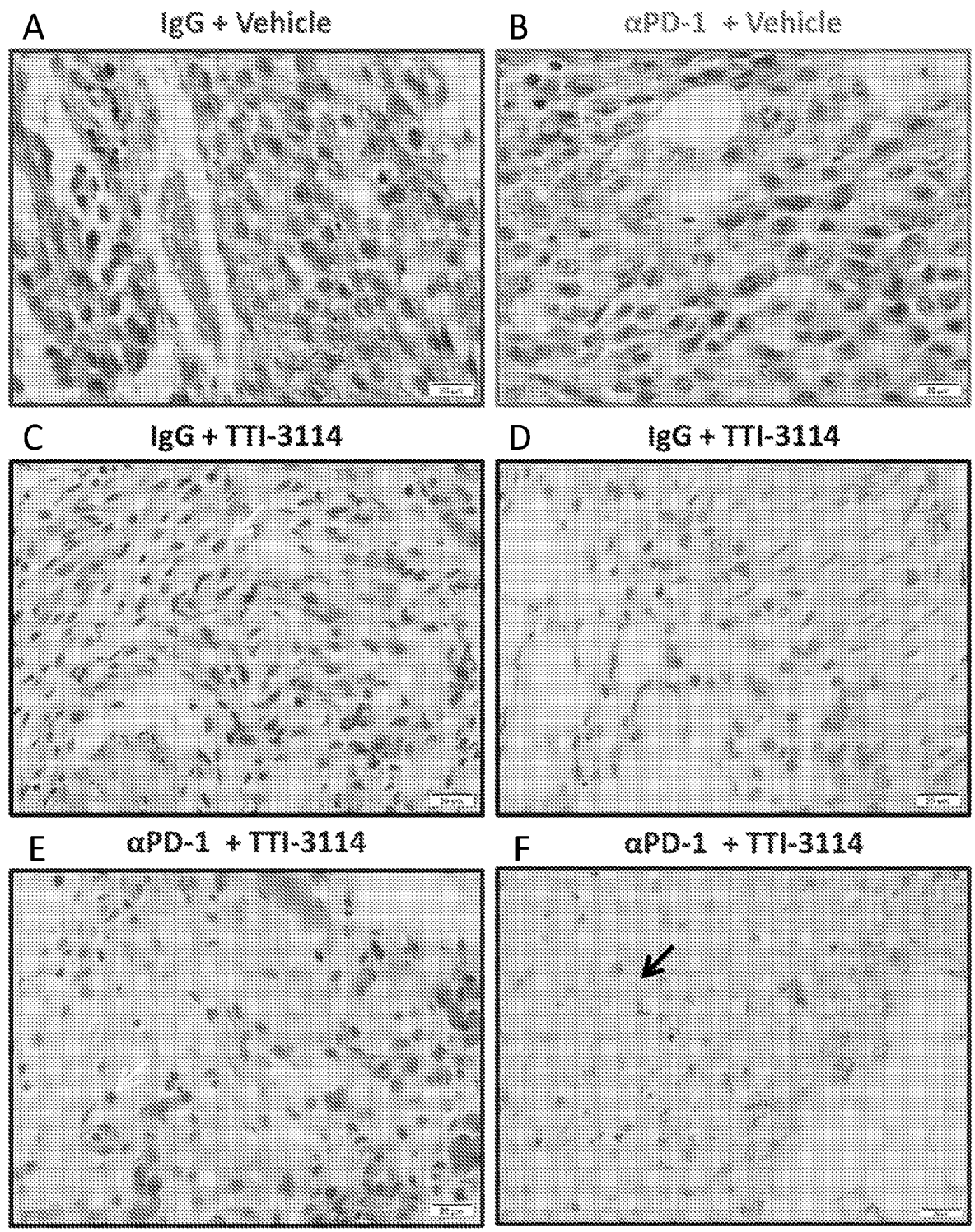
FIG. 4 shows that TTI-3114 treatment is associated with lymphocytic infiltration. Mice were treated with TTI-3114 according to the scheme in FIG. 2A. Representative images from H&E stained sections of formalin fixed tumors (A-B) or regressed lesions (C-F) harvested at day 6. (A-B) Sheets of pleomorphic melanocytes with pigment (brown) characteristic of melanoma. (C-D) Residual tumor with lymphocytic infiltrates from two separate mice. (E-F) Residual necrotic tumors with small nuclear fragments of irregular shape and size with presence of lymphocytes. 40×, scale bar represents 20 µm, grey arrows indicate lymphocytes, black arrow indicates pink nuclei of necrotic cells.

Tumors or regressed lesions were harvested from tumor-bearing mice were treated with αPD-1 in combination with TTI-3114 at day 6 and were investigated for lymphocytic infiltration. Sections from formalin fixed tumors (FIGS. 4A-B) and regressed lesions (FIGS. 4C-F) were H&E stained. Sheets of pleomorphic melanocytes with pigment (brown staining) characteristic of melanoma were seen in tissues from mice treated with a control IgG and in tissues from mice treated with αPD-1 (FIGS. 4A-B). Following treatment with αPD-1 in combination with TTI-3114, residual tumor with lymphocytic infiltrates (FIGS. 4C-D) and residual necrotic tumors with small nuclear fragments of irregular shape and size with presence of lymphocytes (FIGS. 4E-F) were seen. Thus, TTI-3114 treatment is associated with lymphocytic infiltration.

Schweinfurthin-Induced Tumor Regression is Immune-Dependent

Figure 5:
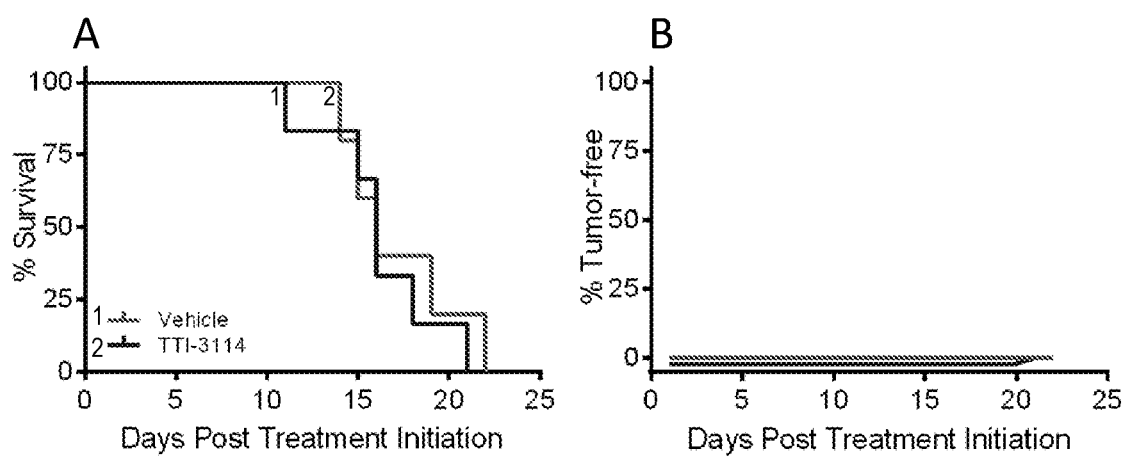
FIG. 5 shows that Schweinfurthin-induced tumor regression is immunedependent. Immunocompromised NSG mice with established B16.F10 tumors were treated with TTI-3114 or Vehicle control as defined in FIG. 2A. (A) Kaplan-Meier survival analysis. (B) The percentage of mice tumor-free (no palpable or visually apparent tumor) in each treatment group. N=6/group; no significant differences. Data are representative of two independent experiments.

Immunocompromised NSG mice with established B16.F10 tumors were treated with TTI-3114 or vehicle control as defined in FIG. 2A. A Kaplan-Meier survival analysis showing survival is shown in FIG. 5A. The percentage of mice that were tumor-free (having no palpable or visually apparent tumor) in each treatment group is shown in FIG. 5B.

Example 2: Schweinfurthin Compounds Combine with Anti-PD-1 Immunotherapy to Control Established Murine Melanoma Experiments are performed using the most efficacious dose, regimen, and ICI from those provided in Example 1. An overview of the experimental design is provided in FIG. 2.

In one experiment, animals are implanted with tumor as described herein. 5 groups of 8 animals each (TTI-7106 via IP route, TTI-7106 via SC route, TTI-7106 IP+antibody, TTI-7106 SC+antibody, and antibody alone) are used. The antibody is given by the IP route.

In another experiment, 4 groups of 12 animals are used. Tumors are implanted and dosing begins as in previous experiments. The anti-PD-1 antibody is used for these experiments and will use the 5-day treatment with the most efficacious dose of TTI-7106 (TTI-7106 for 5 days, vehicle 5 days, TTI-7106 5 days+anti-PD-1 antibody days 1, 4, and 8, and anti-PD-1 antibody alone on days 1, 4, and 8). Tumors and spleens are harvested from the animals on days 3, 6, and 10 in groups of 4 animals from each group.

For each experiment, 50-100 μL of blood is drawn from each animal in all experiments at days −1, 6, and 28 (measured from treatment initiation) by mandibular venipuncture procedure. The blood sample is split with 50 μL used for bioanalytical measurement of the drug concentration, and the remainder is used to for immune profiling.

Experimental Design:

TTI-7106 is used for these experiments near the maximum tolerated dosage (MTD) of 40 mg/kg. Given the low toxicity seen at 30 mg/kg of TTI-4242 (these two drugs have nearly identical MTD), increasing the dosage is likely to have a higher impact on tumor growth and will still be well tolerated. TTI-7106 is authenticated in batches based on the NMR spectroscopy and mass spectrometry. All experiments are carried out on equal groups of male and female mice.

In Vivo Efficacy and Mechanism Experiments:

Using the B16.F10 murine melanoma model in immunocompetent mice, treatment regimens of schweinfurthin analog vs. +/− anti-PD-1 therapy are optimize. For these experiments, groups of 8-week old C57BL/6J mice are implanted with $1 \times 10^5$ freshly cultured B16.F10 tumor cells subcutaneously in the left flank. Mice are monitored for the development of tumors and when palpable randomized into one of 8 groups (anti-PD-1 (clone RMP1-14; BioXCell) or control rat IgG (Sigma) at 200 μg/day intraperitoneally twice per week, TTI-7106(30 mg/kg for five days)+control IgG, and TTI-7106 (30 mg/kg for five days)+anti-PD1, TTI-7106 (40 mg/kg for five days)+control IgG, TTI-7106 (40 mg/kg for five days)+anti-PD1, TTI-7106(40 mg/kg for 28 days)+control IgG, and TTI-7106 (40 mg/kg for 28 days). All drugs are given by intraperitoneal injection to test if increasing dosage of TTI-7106 is tolerated in combination with the anti-PD-1 antibody, and if extended treatment duration leads to increased efficacy in this model. The most efficacious dosage regimen is used to test the schweinfurthin compound in combination with anti-CTLA-4 antibody. This experiment has 4 groups based on the most efficacious compound dose and schedule as determined in the initial experiment. The groups are TTI-7106+IgG, TTI-7106+anti-CTLA-4, IgG alone, and anti-CTLA-4 alone. The groups include 8 animals/group. Mice receive the anti-PD-1, anti-CTLA-4 and IgG for 3 weeks in all groups. Tumors are measured every 2 days using digital calipers and the tumor volume calculated as (length×width$^2$)/2.

Bioanalytical Assessment of Drug Plasma Concentration:

To determine plasma concentrations of drug responsible for drug effects HPLC with MS/MS or fluorescence detection are used to measure drug. Plasma samples are processed by solid supported liquid-liquid extraction on SLE columns (Biotage SPE+1 mL) with organic phase elution using ethyl acetate or chloroform as appropriate. Eluents are dried under argon stream and reconstituted into acetonitrile for analysis. Samples are analyzed by API-ES MS with negative ionization using a Waters UPLC/MS Aquity system. Molecular ions (M-H) for similar compounds are readily observable using these parameters. Compound quantification is followed by multiple reaction monitoring of a selected MS/MS fragment. Alternatively, these compounds are observable by fluorescence which could also be used as the detection method.

Immune Profiling:

Multicolor flow cytometry of immune cells obtained from blood, tumors and lymphoid tissues are performed as described elsewhere (see, e.g., Cozza et al., 2015 *Cancer Immunology Immunotherapy*, 64:325-336; and Ward-Kavanagh et al., 2014 *Cancer Immunology Research*, 2:777-788). For blood samples, 100 μl of fresh blood is blocked with anti-CD16/CD32 for 15 minutes at room temperature to block Fc receptors followed by incubation with antibodies to mouse lymphocyte cell surface molecules (CD45.2, CD3, NK1.1, CD19, γδTCR, CD4, CD8α, CD44, CD62L, CD25, PD-1, CD137) at predetermined dilutions for 15 minutes at room temperature. Red blood cells are lysed by addition of tris-buffered ammonium chloride for 5 minutes at 37° C. Cells are washed twice with PBS containing 2% fetal bovine serum and 0.01% sodium azide (FACS buffer) and then stained with 7-amino actinomycin D to identify dead cells prior to evaluation using a 16-color Becton Dickinson LSRFortessa flow cytometer. Tumors and spleens will be processed to single cell suspensions as described elsewhere (see. e.g., Ward-Kavanagh et al., 2014 *Cancer Immunology Research*, 2:777-788), with tumors first undergoing digestion with a collagenase/DNAse mixture. Cell suspensions are stained first with the fixable live/dead cell stain Zombie Yellow for 15 minutes at room temperature in PBS prior to addition of anti-CD16/CD32 for another 15-minute incubation. Parallel samples are then stained for lymphocytes as above or for myeloid cells using the following multicolor panel and gating strategy: $CD3^+$, $NK1.1^+$ and $CD19^+$ lymphocytes will be excluded from the live, $CD45.2^+$ population prior to evaluation of cells expressing surface markers associated with subsets of macrophages and dendritic cells (CD11b, CD11c, Ly6C, Ly6G, F4/80, MHCII, B220, CD8α). Cells are fixed in 2% paraformaldehyde prior to data collection using a 16-color Becton Dickinson LSRFortessa flow cytometer and data analyzed using FlowJo V10.4 software.

Statistical Analysis:

For all of these studies either bioluminescent readout of tumor size, or caliper measurement of tumor size are used. Use of 8 animals per group enables detection of a standardize effect size (i.e., a mean difference in the unit of common standard deviation either photon count or tumor volume) of about 1.6 with at least 81% statistical power (alpha level is Bonferronni-corrected to be 0.0167). For efficacy studies, the main outcome variable is tumor growth. Outcome variables Two-way ANOVA models are used and Tukey's test is used for the pairwise comparisons following the ANOVA. For the immunotherapy models differences in tumor growth curves are evaluated by linear mixed models for longitudinal analysis and Kaplan-Meier survival curves are evaluated by log rank test. All data is analyzed using Prism software version 5f or higher or SAS version 9.4.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cancer, wherein said method comprises administering TTI-4242 or a pharmaceutically acceptable salt thereof and an anti-PD-1 antibody to said mammal, wherein said TTI-4242 or said pharmaceutically acceptable salt and said anti-PD-1 antibody are administered to said mammal within 3 days of each other, and wherein the number of cancer cells within said mammal is reduced.

2. The method of claim 1, wherein said mammal is a human.

3. The method of claim 1, wherein said cancer is a melanoma.

4. The method of claim 1, wherein said TTI-4242 or said pharmaceutically acceptable salt and said anti-PD-1 antibody are administered to said mammal simultaneously.

5. The method of claim 1, wherein said TTI-4242 or said pharmaceutically acceptable salt and said anti-PD-1 antibody are administered to said mammal at different times.

6. The method of claim 5, wherein said TTI-4242 or said pharmaceutically acceptable salt are administered to said mammal before said anti-PD-1 antibody are administered to said mammal.

7. The method of claim 5, wherein said TTI-4242 or said pharmaceutically acceptable salt are administered to said mammal after said anti-PD-1 antibody are administered to said mammal.

8. A method for reducing risk of developing cancer in a mammal, wherein said method comprises administering TTI-4242 or a pharmaceutically acceptable salt thereof and an anti-PD-1 antibody to said mammal, wherein said TTI-4242 or said pharmaceutically acceptable salt and said anti-PD-1 antibody are administered to said mammal within 3 days of each other, and wherein time to developing cancer within said mammal is increased as compared to time to developing cancer within a control mammal not administered said TTI-4242 or said pharmaceutically acceptable salt and said anti-PD-1 antibody.

9. The method of claim 8, wherein said mammal is a human.

10. The method of claim 8, wherein said TTI-4242 or said pharmaceutically acceptable salt and said anti-PD-1 antibody are administered to said mammal simultaneously.

11. The method of claim 8, wherein said TTI-4242 or said pharmaceutically acceptable salt and said anti-PD-1 antibody are administered to said mammal at different times.

12. The method of claim 11, wherein said TTI-4242 or said pharmaceutically acceptable salt are administered to said mammal before said anti-PD-1 antibody are administered to said mammal.

13. The method of claim 11, wherein said TTI-4242 or said pharmaceutically acceptable salt are administered to said mammal after said anti-PD-1 antibody are administered to said mammal.

14. A composition for treating cancer, said composition comprising TTI-4242 or a pharmaceutically acceptable salt thereof and one or more anti-PD-1 antibodies.

* * * * *